(12) United States Patent
Polidoro

(10) Patent No.: US 10,808,964 B2
(45) Date of Patent: Oct. 20, 2020

(54) WALL MOUNTED HOSPITAL BED, HEALTH CARE FACILITY, OR OTHER WALL (OR SURFACE) TYPE LIGHT WITH ULTRAVIOLET-C GERMICIDAL (OR OTHER) AIR DECONTAMINATION SYSTEM

(71) Applicant: John Polidoro, Bensalem, PA (US)

(72) Inventor: John Polidoro, Bensalem, PA (US)

( * ) Notice: Subject to any disclaimer, the term of this patent is extended or adjusted under 35 U.S.C. 154(b) by 0 days.

(21) Appl. No.: 15/589,548

(22) Filed: May 8, 2017

(65) Prior Publication Data

US 2017/0321877 A1 Nov. 9, 2017

Related U.S. Application Data

(60) Provisional application No. 62/391,681, filed on May 9, 2016.

(51) Int. Cl.
| | |
|---|---|
| *F24F 13/28* | (2006.01) |
| *F21S 8/00* | (2006.01) |
| *F21V 33/00* | (2006.01) |
| *A61L 9/20* | (2006.01) |
| *F24F 7/007* | (2006.01) |
| *F21V 23/04* | (2006.01) |
| *F21V 23/02* | (2006.01) |
| *F21S 9/02* | (2006.01) |

(52) U.S. Cl.
CPC ............ *F24F 13/28* (2013.01); *A61L 9/20* (2013.01); *F21S 8/033* (2013.01); *F21V 33/0088* (2013.01); *F24F 7/007* (2013.01); *A61L 2209/111* (2013.01); *A61L 2209/12* (2013.01); *A61L 2209/14* (2013.01); *F21S 9/02* (2013.01); *F21V 23/02* (2013.01); *F21V 23/0471* (2013.01); *F24F 2221/02* (2013.01); *F24F 2221/17* (2013.01)

(58) Field of Classification Search
CPC .......... A61L 2209/111; A61L 2209/12; A61L 2209/14; A61L 9/20; F21S 8/033; F21S 9/02; F21V 23/02; F21V 23/0471; F21V 33/0088; F24F 13/28; F24F 2221/02; F24F 2221/17; F24F 7/007
See application file for complete search history.

(56) References Cited

U.S. PATENT DOCUMENTS

| | | | | |
|---|---|---|---|---|
| 3,674,421 | A * | 7/1972 | Decupper | A61L 9/20 422/121 |
| 3,757,495 | A * | 9/1973 | Sievers | B01D 46/00 96/121 |
| 3,846,072 | A * | 11/1974 | Patterson | A61L 9/20 96/222 |
| 4,045,192 | A * | 8/1977 | Eckstein | A61G 10/02 96/224 |
| 4,553,992 | A * | 11/1985 | Boissinot | A61L 9/16 126/299 D |

(Continued)

*Primary Examiner* — Tsion Tumebo
(74) *Attorney, Agent, or Firm* — Law Offices of Leo Mikityanskiy, P.C.; Leonid Mikityanskiy

(57) ABSTRACT

A wall- or surface-mounted light fixture with a housing containing one or more external visible light sources to illuminate the space where the light fixture is mounted, one or more UV emitters inside the housing to destroy bacteria and pathogens, and one or more fans inside the housing that recirculate the air in a space and subject the air to the UV radiation inside the housing, destroying bacteria and pathogens in the air passing though the housing.

42 Claims, 5 Drawing Sheets

(56) References Cited

U.S. PATENT DOCUMENTS

| | | | | |
|---|---|---|---|---|
| 4,666,478 | A * | 5/1987 | Boissinot | A61L 9/16 126/299 D |
| 5,112,370 | A * | 5/1992 | Gazzano | A61L 9/20 422/121 |
| 5,225,167 | A * | 7/1993 | Wetzel | A61L 9/20 96/224 |
| 5,632,806 | A * | 5/1997 | Galassi | F24C 15/20 422/24 |
| 5,702,648 | A * | 12/1997 | White | B01F 3/022 261/142 |
| 5,891,399 | A * | 4/1999 | Owesen | A61L 9/20 422/121 |
| 5,987,908 | A * | 11/1999 | Wetzel | F24F 1/027 62/259.1 |
| 5,997,619 | A * | 12/1999 | Knuth | A61L 9/20 55/356 |
| 6,062,977 | A * | 5/2000 | Hague | A61G 13/108 454/341 |
| 6,264,888 | B1 * | 7/2001 | Palestro | A61L 9/20 422/24 |
| 6,302,783 | B1 * | 10/2001 | Vroege | F24F 3/1603 454/233 |
| 6,328,937 | B1 * | 12/2001 | Glazman | A61L 9/20 422/121 |
| 6,500,387 | B1 * | 12/2002 | Bigelow | A61L 9/20 250/432 R |
| 6,619,063 | B1 * | 9/2003 | Brumett | F24F 3/153 62/259.1 |
| 6,855,295 | B2 * | 2/2005 | Kulp | F24F 3/16 422/121 |
| 7,005,111 | B2 * | 2/2006 | Bollini | A61L 9/20 250/455.11 |
| 7,037,188 | B2 * | 5/2006 | Schmid | A47C 21/044 454/187 |
| 7,251,953 | B2 * | 8/2007 | Wetzel | F24F 3/161 62/419 |
| 8,350,228 | B2 | 1/2013 | Welker | |
| 8,398,264 | B2 | 3/2013 | Anderson et al. | |
| 8,439,517 | B2 | 5/2013 | Welker | |
| 9,310,088 | B2 * | 4/2016 | Melikov | A61G 10/02 |
| 9,517,280 | B2 | 12/2016 | Lynn et al. | |
| 2002/0098127 | A1 * | 7/2002 | Bollini | A61L 9/20 422/121 |
| 2003/0217641 | A1 * | 11/2003 | Palestro | A61L 9/20 95/273 |
| 2006/0213157 | A1 * | 9/2006 | Kalous | F24F 3/1603 55/385.2 |
| 2012/0085927 | A1 * | 4/2012 | Maeng | A61L 9/20 250/454.11 |

\* cited by examiner

WALL MOUNTED HOSPITAL BED, HEALTH CARE FACILITY, OR OTHER WALL (OR SURFACE) TYPE LIGHT WITH ULTRAVIOLET-C GERMICIDAL (OR OTHER) AIR DECONTAMINATION SYSTEM

This patent application claims priority to provisional patent application Ser. No. 62/391,681, filed on May 9, 2017, which is hereby incorporated by reference in its entirety.

This invention was not made pursuant to any federally-sponsored research and/or development.

THE FIELD OF INVENTION

Dangerous bacteria, viruses, and other pathogens are present in the air and on various physical surfaces, which are easily spread through air and by contact with contaminated surfaces. These airborne or surface pathogens, which are more common in hospitals and other health care facilities, can cause infections in people, where the patients frequently have other diseases, lowered immune system responses, respiratory disorders, and conditions prone to infection. Methods of control are difficult and labor-intensive, involving washing or wiping surfaces with caustic germicidal substances, leaving a film and/or smell of these substances on surfaces. An even greater problem was disinfecting the air to destroy airborne bacteria and other pathogens that could resettle on surfaces.

The present invention is a wall- or surface-mounted luminaire (light fixture) with an internal air decontamination system. The light fixture is mounted above a hospital bed, in a health care facility, or on a similar wall or surface at a similar facility, preferably utilizing Ultraviolet-C germicidal source for the air decontamination system. This self-contained decontamination light fixture is designed to kill airborne pathogens that enter into the light fixture's internal decontamination chamber. This system is intended to be mounted to walls or surfaces, preferably above hospital beds, or in other similar areas and in other facilities, that will allow the system to draw room air from the room, and preferably from directly above bed and the patient, or other areas of concern, and into the unit's decontamination chamber.

However, the system and device of the present invention may be mounted on any wall or surface, at ay height, without detrimental impact to its efficiency or operation, such as, for example, directly to a ceiling or just above the floor level to provide floor-level lighting, while at the same time decontaminating the air in the room. In case of such mounting, the system may be even more efficient in combating bacteria and pathogens near the floor level, brought in by people's shoes from the outside.

BACKGROUND OF THE INVENTION

The benefits of devices that use ultraviolet spectrum light for killing bacteria and other pathogens are known in the art. Non-visible, Ultraviolet C or Germicidal light source technology is known to destroy the DNA or ability of bacteria and other pathogens to reproduce. Visible light utilized on common light fixtures used as a light source is usually in the 400-700 nm range. UV light used to destroy bacteria and other pathogens is typically below 390 nm (although any light below 400 nm is considered UV light). Some of the methods of using UV light for killing bacteria, including dangerous staphylococcus strains, are disclosed in U.S. Pat. Nos. 8,350,228, 8,398,264, 8,439,517, and 9,517,280, the disclosures of which are incorporated herein by reference.

U.S. Pat. Nos. 8,350,228 and 8,439,517, in particular, perform the disinfecting function by way of a germicidal modular insert or a modular insert adder box incorporating UV emitters, attached to a recessed grid or inverted T-bar ceiling troffer-type light fixture. The recessed troffer-type light fixture of the '228 patent typically rests on inverted T-bar grid suspended ceiling in a building, replacing panels in the suspended ceiling. The light fixture of the '228 patent includes a luminaire with a germicidal modular insert affixed to the inverted T-Bar ceiling grid. The '228 patent requires a pivotal relationship between the unit and the ceiling grid, with first position having the same planar surface as the ceiling during operation of the light fixture and the second position pivoted 90 degrees from ceiling for light fixture maintenance or access to germicidal modular insert UV tube replacement. However, that particular approach is less impractical and dangerous during installation or maintenance because heavy, recessed inverted T bar ceiling-mounted light fixtures require disengagement from the mounting surface to pivot 90 degrees, below ceiling surface for service or maintenance in a manner which is unsafe and may cause the unit to break free from its attachment means, injuring the service technician or maintenance person, disconnecting from the power supply connection, or causing damage to the installation facility. The increased weight differential of the unit in the '228 patent from the original standard recessed troffer light fixture may require additional ceiling support versus the original.

What is needed is an easily- and safely-mounted light fixture, which grants easy access to the lights and internal components for maintenance, repair and replacement, utilizes the existing power supply source, and which efficiently disinfects the air passing (circulating) through the light fixture, destroying the bacteria in the air.

The present invention solves this problem by providing a wall- or surface-mounted light fixture that recirculates the air and subjects the air to UV radiation inside the light fixture, destroying many kinds of harmful bacteria. The present invention relates more particularly to a system and device that includes a housing attachable to a wall or a surface, one or more UV emitters inside the housing, and one or more fans inside the housing that recirculate the air in a room and subject the air to the germicidal UV radiation inside the housing, thereby destroying bacteria.

SUMMARY OF THE INVENTION

It is an object of the present invention to provide a securely-mounted light fixture that includes a housing attachable to a wall or a surface, one or more external visible light sources on the surface or protruding through the housing to illuminate the space where the light fixture is mounted, or more UV emitters inside the housing to destroy pathogens, and one or more fans inside the housing that recirculate the air in a room and subject the air to the UV radiation inside the housing, destroying bacteria and pathogens in the air passing though the housing. The light fixture may optionally include an external UV emitter for decontaminating the area directly (both the surfaces of the area and the air).

The external visible light sources of the system and device of the present invention may be of 405 nm wavelength, for example, which is in the visible light spectrum. The internal and optional external decontamination sources (UV emitters) preferably range from 100 nm to 400 nm.

The light fixture is a completely self-contained air decontamination unit, preferably with an anti-microbial finish, that requires no additional devices other than a power supply (currently AC). This light fixture uses internal fans or other mechanisms known in the art to draw room air into one end of the light fixture and expel the air from the other end of the light fixture to return the disinfected air to the room. As the air passes through the light fixture, the air flows by one or more Ultraviolet germicidal light sources which destroy organisms and pathogens that come into contact with the germicidal light source emissions, decontaminating the air before the air exits the light fixture. This system and device are unique because, once installed, the light fixture decontaminates the air in a room cavity and does not require moving or altering the installation in any way, other than periodically opening the designed access panel for maintenance. All maintenance is performed by way of a convenient maintenance access system, designed for quick access to replaceable components, which is safer than maintenance of overhead (T-Bar ceiling-mounted) light fixtures.

Some of the features of the system and device of the present invention include: this wall or surface mounted luminaire with internal air decontamination system may be permanently or detachably affixed to mounting surface; it may not required to disengage from the mounting surface for maintenance or servicing; this wall or surface mounted luminaire with internal air decontamination system may be mechanically fastened to a wall or a surface in a way that does not require the luminaire to be moved or disengaged from mounting position for maintenance or service; this wall or surface mounted luminaire with an internal air decontamination system is designed to operate as a primary, secondary, or part of facility room or area lighting system; this luminaire is designed to pull room air into the unit, where the room air flows into the unit internal decontamination chamber and where the air pathogens are destroyed before the air exits the unit exhaust provision; this luminaire contains room lighting (the external visible light source) and internal non-visible light source; the optional external non-visible light source may consist of Light emitting diode (LED), fluorescent, germicidal, ultraviolet light, ultraviolet-C light (UV-C), or other decontamination-type source, just as the internal non-visible light source may.

This wall or surface mounted luminaire with internal air decontamination system has option to switch from external visible light source to external non-invisible light source. External non-visible light source consist of germicidal or ultraviolet light (UV-C) designed to destroy pathogens on surfaces or in air as they come into contact with external non-visible light source. This luminaire with an internal air decontamination system and an external non-visible light source preferably has wavelengths ranging from 100 nm to 400 nm. The wall or surface mounted luminaire is preferably accessible for maintenance by an access method that does not require unit to be moved, altered, or removed in any way from its mounted position on wall or surface, such as by employing an access panel.

The luminaire may have light switching capabilities, accessible to patient or others near unit, that allow the external visible light source to be controlled directly from unit by switches installed on the device. The unit's external visible light source may be designed as 2-way (On/Off) or as 3-way room lighting consisting of at least two light external visible light sources operating independently or together (3-way room lighting meaning 3-position lighting plus the "off" position). Thus, Position 1: Only one external visible room light source ON position (Light A is On position/Light B is off position); Position 2: Only one external visible room light source ON position (Light B is On position/Light A is Off position); Position 3: Both external visible room light sources ON position (Light A is On position/Light B is On position); Position 4: All external visible room light sources Off position.

The luminaire with internal air decontamination system may contain air filter systems for air decontamination, which may be accessible for maintenance by way of vent cover, grill, or access panel that is removable, hinged, or using other methods that do not require the unit to be moved, removed, pivoted, hinged, altered, or removed or relocated in any way from its installed mounted operating position.

This luminaire preferably has an access cover that does not require the unit to be moved, removed, pivoted, hinged, altered, or removed or relocated in any way from installed mounted operating position for unit maintenance or any reason. This wall or surface mounted luminaire preferably has a switch to shut down power to the internal decontamination chamber when the maintenance panel or access cover of any sort is opened or removed for access or maintenance.

This wall or surface mounted luminaire system consists of any form of pathogen killing, disinfecting, germicidal, or other method or source available. This wall or surface mounted luminaire with internal air decontamination system is capable of being connected to another unit to increase unit linear size (length), or continuous run and also share power supply internally through unit internal raceway (i.e., a modular configuration). This luminaire may contain components designed for easy maintenance by using male/female modular-type connectors or other similar devices.

This luminaire may have occupancy sensors, thermal sensor, or motion sensor devices to control lighting and/or air decontamination system when the room is occupied versus unoccupied. The sensor may be passive infrared, ultrasonic, dual passive infrared and Ultrasonic or other type of sensors known in the art. This luminaire is preferably capable of dimming the external visible light source(s), and the luminaire preferably contains an indicator light to confirm when the internal air decontamination system is or is not working properly or requires maintenance. This wall or surface mounted Luminaire with internal air decontamination system may include an option for a timer system to be used when the external non-visible light source is in use.

This luminaire preferably includes an online or other type monitoring system, on site or remote, which alerts installation facility or others that system that is working properly or is not working properly and requires maintenance. This wall or surface mounted luminaire preferably includes a warning strobe light, flashing light, audible alarm, and/or another warning device, or combination of warning devices, when the unit switches from external visible light source to the optional external non-visible light source (UV) for room decontamination.

BRIEF DESCRIPTION OF THE DRAWINGS

A system and device for disinfecting air in a hospital, health care, or similar facility will now be described by way of example with reference to the accompanying drawings in which.

DESCRIPTION OF THE PREFERRED EMBODIMENT

Figure 1:
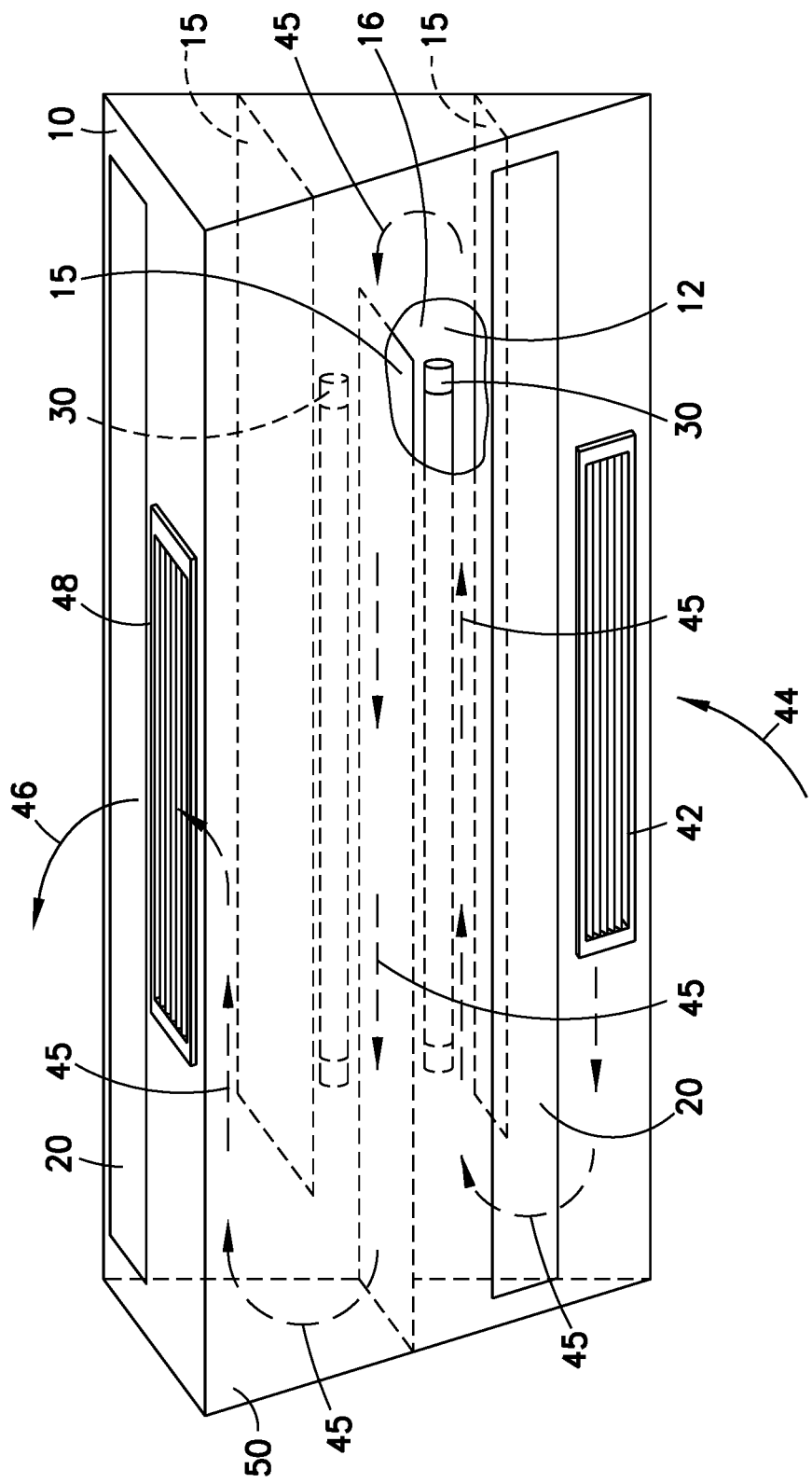
FIG. 1 is a front perspective view of the light fixture of the present invention.

It is an object of the present invention to provide a wall- or surface-mounted luminaire with an internal decontamination system, preferably with a lower level air induction and upper level exhaust, which creates air movement through the luminaire to circulate room air effectively when the unit is wall- or surface-mounted. This luminaire with an internal decontamination system draws air into system from a mid-room level, disinfects the air inside the luminaire housing (enclosure), and exhausts decontaminated air to room upper level is different from the unit exhaust level when wall mounted. Alternatively, the lower level air induction and upper level exhaust may be replaced with an air induction and air exhaust substantially in the same plane, such as for example, in a ceiling-mounting recessed light fixture (drawing the air upward into the air induction and exhausting the air downward into the room from the exhaust).

A wall- or surface-mounted (or recessed) luminaire with an internal decontamination system is provided. The luminaire is designed for wall or surface mounting in areas such as hospitals, health care facilities, and other locations where wall-mounted lighting or surface-mounted (or recessed) lighting is required. Such a luminaire would be useful in hospitals, healthcare and other facilities, where the light source is mounted to the wall above the bed or to ceiling surface (or recessed).

Externally the luminaire contains one or more of external visible light sources as primary or secondary room illumination. The external visible light sources may be Light Emitting Diode (LED), Fluorescent, or other available visible light sources capable of illuminating a room effectively.

Internally, the luminaire contains an internal decontamination system that is designed to draw room air into the fixture's decontamination chamber, where a decontamination source (Ultraviolet-C, Germicidal, or other source) kills airborne pathogens in the room air as the air travels through the system's internal decontamination chamber. The decontaminated air exits the decontamination chamber and exits the unit back into the room.

The luminaire may also contain an external non-visible decontamination light source consisting of germicidal ultraviolet light (UV-C) or similar in function source, designed to destroy pathogens on surfaces or in air as they come into contact with the external non-visible light source. The external non-visible light source may consist of Light emitting diode (LED), fluorescent, germicidal, ultraviolet (UV-C), or any other decontamination source.

Both the internal and the optional external decontamination source are preferably "invisible light" less than 400 nm in wavelength. The lighting may be LED, fluorescent, germicidal, ultraviolet (UV-C), or other decontamination-type source or other lighting known in the art.

Currently, Fluorescent UV-C (Ultraviolet-C) is the most effective decontamination system on market, and the preferred wavelength for the application is 257 nm. UV-C is a pathogen-killing light source that is unsafe for human contact. A decontamination source using UV-C Fluorescent-type is not visible light, so it would be dangerous to humans if not treated safely. However, other methods of destroying bacteria, such as sound or ultrasound technology may be used to destroy pathogens. In that case, the decontamination source would not be light (UV spectrum based), but sound based, and implementing the system and device of the present invention would simply involve replacing the UV-based decontamination source with the sound- or ultrasound-based decontamination source.

Figure 3:
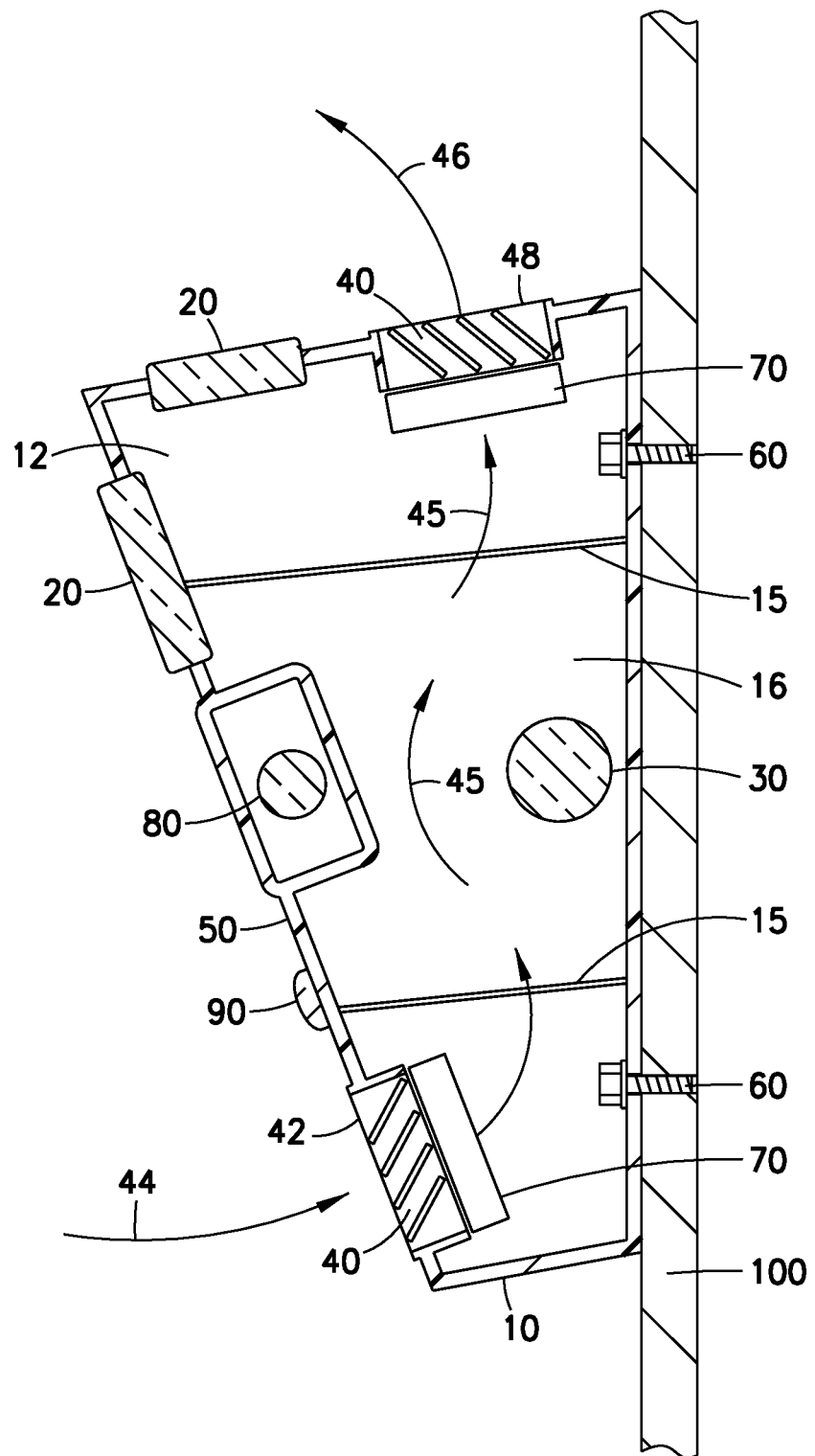
FIG. 3 is a side cross sectional view of the alternative embodying of the light fixture of the present invention illustrated in FIG. 2.

With reference to FIG. 1 and FIG. 3, the preferred embodiment of the present invention achieves this goal with a housing 10, which may be substantially triangular or trapezoidal in the cross section for easier wall mounting and air circulation. The housing 10 is adapted to be placed, attached or mounted onto a wall 100 or a surface inside a room by securing means 60 attached to or mounted on the housing 10. The securing means 60 may be permanently or removably attached to the housing 10 by a variety of methods: glue, screws, bolts, rivets, or the securing means may be permanently attached to the housing 10 by being molded into the material from which the housing 10 is constructed, or welded or riveted to it.

The housing 10 has an internal space 12, in which the internal components of the luminaire are mounted, including one or more external light sources 20 coupled with the housing 10 so that the illuminating part of the light sources 20 is visible outside. The external light sources 20 are preferably selectively operable to illuminate the room or any environment where the luminaire is mounted. The internal space 12 also contains at least two, but possibly more than two, substantially horizontal plates 15 disposed in the internal space 12, defining a decontamination chamber 16 between the plates 15. The plates 15 preferably shield the rest of the internal space 12 and the housing 10 from the UV radiation harmful to people. The plates 15 are preferably substantially parallel to each other, but they do not have to be horizontal: depending on the structure of the internal space 12, the plates 15 may be substantially vertical or other positions.

At least one internal decontamination source 30 is placed, attached or mounted into the decontamination chamber 16 located inside the internal space 12 of the housing 10. Also contained in the internal space 12 of the housing 10 are the means for driving air 40 through the decontamination chamber 16, wherein the air is disinfected by the at least one internal decontamination source 30 when the air passes through the decontamination chamber 16. The means for driving air 40 are preferably air fans, but they could be other means for driving air. Thus, with reference to FIG. 1-3, the means for driving air 40 take room air into the internal space 12 of the housing 10, through the lower air vent 42 and drive it into the decontamination chamber 16 between the plates 15. When the at least one internal decontamination source 30 is active, pathogens and bacteria are killed or disabled when passing through the decontamination chamber 16.

The means for driving air 40 then exhaust disinfected air from the internal space 12 of the housing 10 through the upper air vent 48. The means for driving air 40 may include optional air filters 70, such as, for example particular matter filters, as illustrated in FIG. 3. The directional arrows 44 show the path of air flow that comes into the lower air vent 42, and the directional arrows 46 show the path of the air flow that comes out of the upper air vent 48. The directional arrows 45 show the path of the turbulent air flow through the decontamination chamber 16. The lower air vent 42 and/or the upper vent 48 may be removable or hinged to enable easy access to the air filters 70 for maintenance and/or replacement.

The housing 10 preferably includes a front access panel 50 or another access panel that would be easy to operate for maintenance and repairs of the luminaire, without the need to remove it from its place or permanent or semi-permanent attachment. An access panel 50 in the front or in the side of the housing 10 should generally be convenient.

Figure 2:
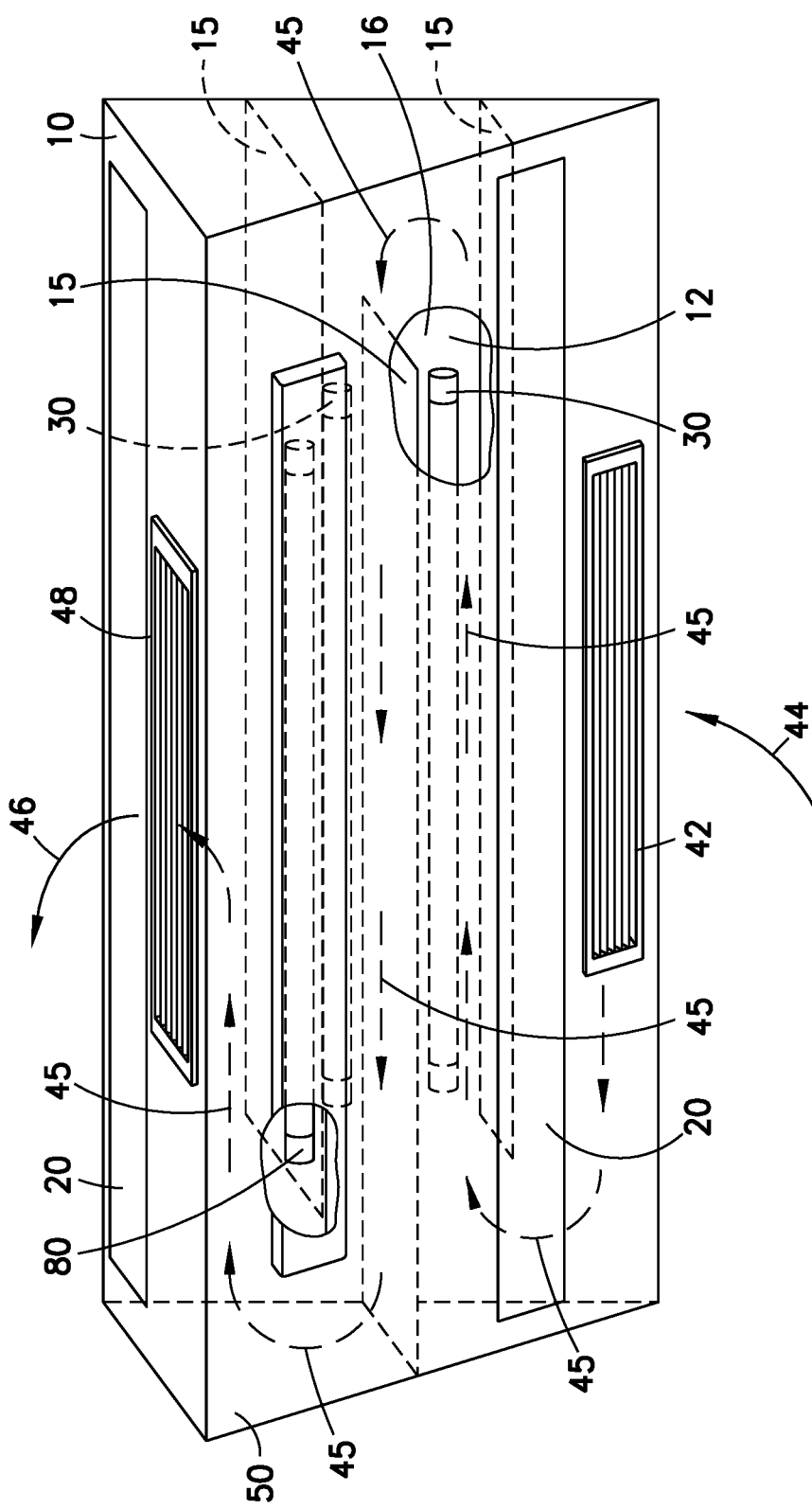
FIG. 2 is a front perspective view of an alternative embodying of the light fixture of the present invention.

An alternative embodiment of the system and device of the present invention is illustrated in FIG. 2. With reference to FIG. 2, this alternative embodiment of the present invention has a housing 10, which is substantially triangular in the cross section for easier wall mounting and air circulation. The housing 10 is adapted to be placed, attached or mounted onto a wall 100 or a surface inside a room by securing means 60 attached to or mounted on the housing 10, as illustrated in FIG. 3. The securing means 60 may be permanently or removably attached to the housing 10 by a variety of methods: glue, screws, bolts, rivets, or other means, or the securing means 60 may be permanently attached to the housing 10 by being molded into the material from which the housing 10 is constructed, or welded or riveted to it. Any combination of the disclosed attachment methods may be used, and the actual securing means 60 used on the housing 10 determines the connection to the wall 100 (for example, bolts are bolted in and screws are screwed in—preferably into aluminum or wooden beams, or other structures that can support the weight of the luminaire).

The housing 10 has an internal space 12, in which the internal components of the luminaire are mounted, including one or more external light sources 20 coupled with the housing 10 so that the illuminating part of the light sources 20 is visible outside. The external light sources 20 are preferably selectively operable to illuminate the room or any environment where the luminaire is mounted. The internal space 12 also contains at least two, but possibly more than two, substantially horizontal plates 15 disposed in the internal space 12, defining a decontamination chamber 16 between the plates 15. The plates 15 preferably shield the rest of the internal space 12 and the housing 10 from the UV radiation harmful to people.

At least one internal decontamination source 30 is placed, attached or mounted into the decontamination chamber 16 located inside the internal space 12 of the housing 10. Also contained in the internal space 12 of the housing 10 are the means for driving air 40 through the decontamination chamber 16, wherein the air is disinfected by the at least one internal decontamination source 30 when the air passes through the decontamination chamber 16. The means for driving air 40 are preferably air fans, but they could be other means for driving air. Thus, with reference to FIG. 2-3, the means for driving air 40 take room air into the internal space 12 of the housing 10, through the lower air vent 42 and drive it into the decontamination chamber 16 between the plates 15. When the at least one internal decontamination source 30 is active, pathogens and bacteria are killed or disabled when passing through the decontamination chamber 16.

The means for driving air 40 then exhaust disinfected air from the internal space 12 of the housing 10 through the upper air vent 48. The means for driving air 40 may include optional air filters 70, such as, for example particular matter filters, as illustrated in FIG. 3. The directional arrows 44 show the path of air flow that comes into the lower air vent 42, and the directional arrows 46 show the path of the air flow that comes out of the upper air vent 48. The directional arrows 45 show the path of the turbulent air flow through the decontamination chamber 16. The lower air vent 42 and/or the upper vent 48 may be removable or hinged to enable easy access to the air filters 70 for maintenance and/or replacement.

The housing 10 preferably includes a front access panel 50 or another access panel that would be easy to operate for maintenance and repairs of the luminaire, without the need to remove it from its place or permanent or semi-permanent attachment. An access panel 50 in the front or in the side of the housing 10 should generally be convenient. This alternative embodiment also includes an external decontamination source 80 mounted on the outside of the housing 10 (or inside the housing but so that the emitting part of the external decontamination source 80 protrudes from the housing 10 to enable decontamination of the immediate area). Because this preferred embodiment employs a substantially triangular or trapezoidal cross section housing 10, the external decontamination source 80 is slanted or tilted naturally towards the lower part of the room or the immediate surrounding area below the luminaire, so that when the external decontamination source 80 is turned on, it destroys bacteria and pathogens in that area. An optional warning strobe 90 may also be mounted in the housing 10, illustrated in FIG. 3 just below the external decontamination source 80. The warning strobe 90 warns people not to come into the room or the immediate surrounding area if the external decontamination source 80 is activated because UV radiation, which is one of the decontamination methods discloses in this application, is harmful to people.

Figure 4:
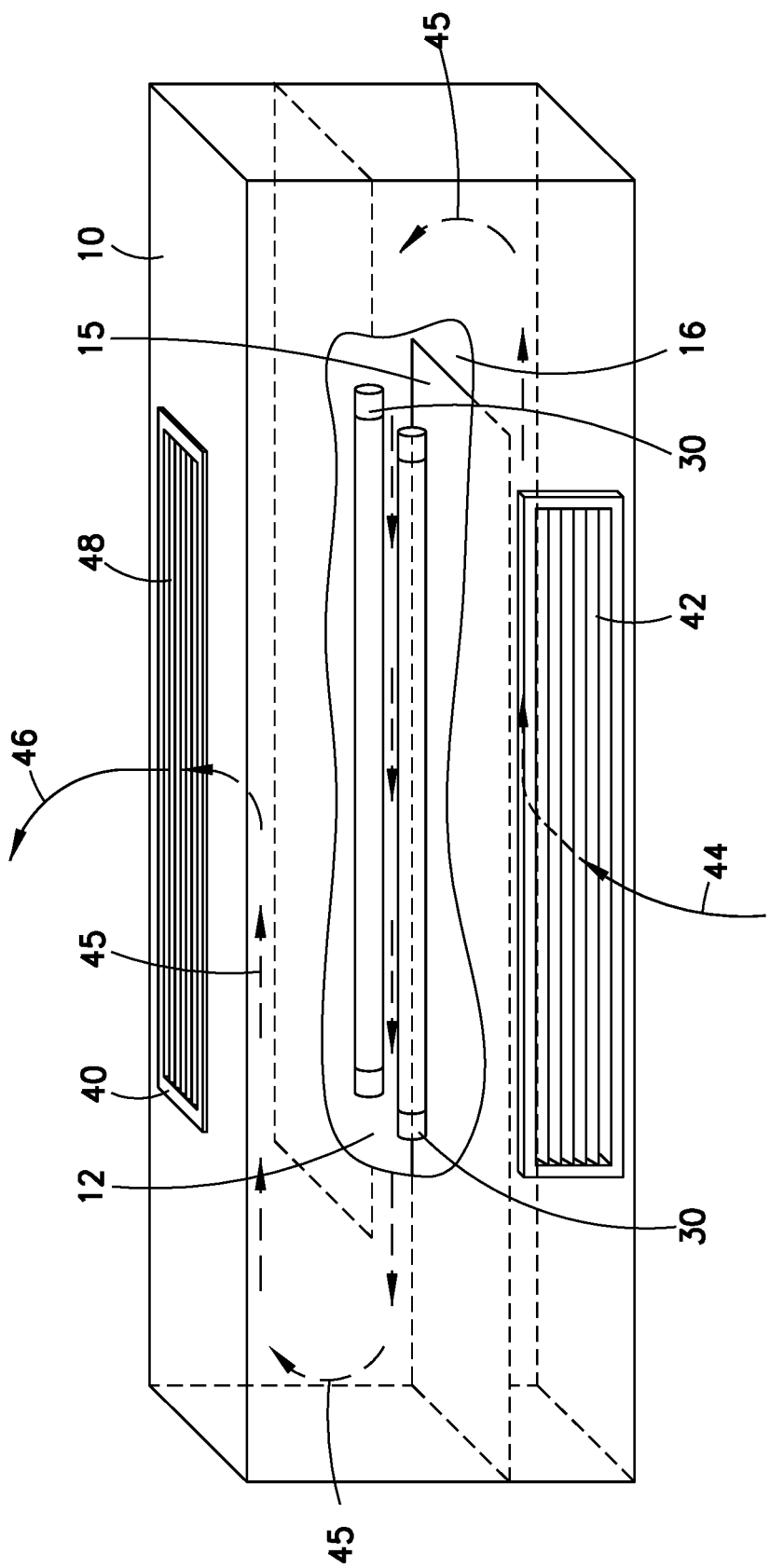
FIG. 4 is a front perspective cross section view of another alternative embodying of the light fixture of the present invention.

Yet another alternative embodiment of the system and device of the present invention is illustrated in FIG. 4. With reference to FIG. 4, this alternative embodiment of the present invention has a housing 10, which is rectangular in the cross section. However, the physical shape of the housing may be of any shape. The housing 10 has an internal space 12, in which the internal components of the luminaire are mounted. The internal space 12 contains at least two, but possibly more than two, substantially horizontal plates 15 disposed in the internal space 12, defining a decontamination chamber 16 between the plates 15. The plates 15 preferably shield the rest of the internal space 12 and the housing 10 from the UV radiation harmful to people.

At least one internal decontamination source 30 is placed, attached or mounted into the decontamination chamber 16 located inside the internal space 12 of the housing 10. Also contained in the internal space 12 of the housing 10 are the means for driving air 40 through the decontamination chamber 16, wherein the turbulent air is disinfected by the at least one internal decontamination source 30 when the air passes through the decontamination chamber 16. The means for driving air 40 are preferably air fans, but they could be other means for driving air. Thus, with reference to FIG. 4, the means for driving air 40 take room air into the internal space 12 of the housing 10, through the lower air vent 42 and drive it into the decontamination chamber 16 between the plates 15. When the at least one internal decontamination source 30 is active, pathogens and bacteria are killed or disabled when passing through the decontamination chamber 16.

The means for driving air 40 then exhaust disinfected air from the internal space 12 of the housing 10 through the upper air vent 48. The directional arrows 44 show the path of air flow that comes into the lower air vent 42, and the directional arrows 46 show the path of the air flow that comes out of the upper air vent 48. The directional arrows 45 show the path of the turbulent air flow through the decontamination chamber 16. The lower air vent 42 and/or the upper vent 48 may be removable or hinged to enable easy access to optional air filters or fan system for maintenance and/or replacement.

Figure 5:
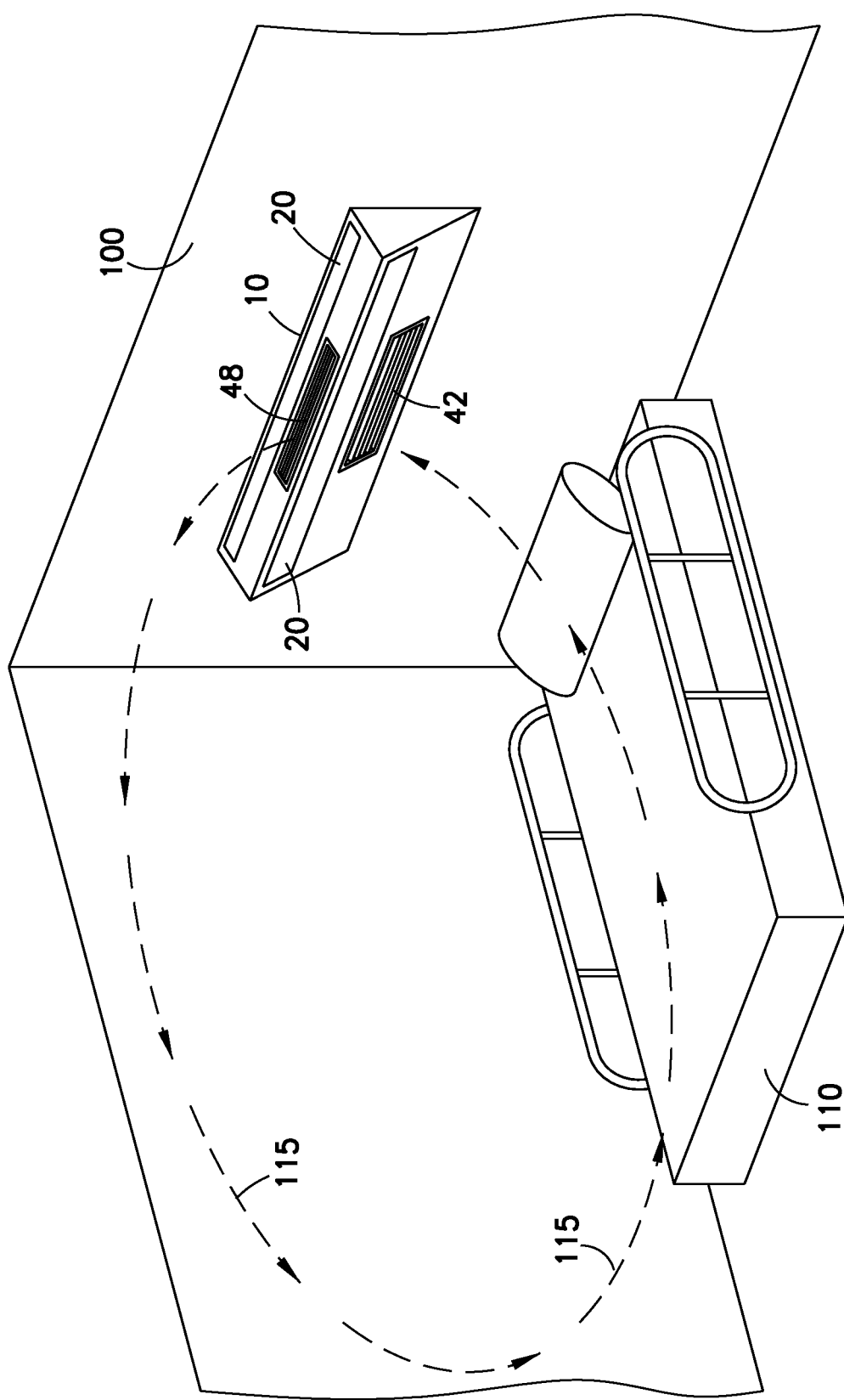
FIG. 5 is a perspective view of the mounting and use of the light fixture of the present invention illustrated in FIG. 1.

The practical use of the preferred embodiment of the present invention is illustrate in FIG. 5, where the light fixture's housing 10 is mounted on a wall 100 above a hospital bed 110. The light fixture circulates the air in the room and above the hospital bed 110 by drawing air into the lower air vent 42, pushing air though the housing 10 where the air is decontaminated as illustrated in FIGS. 1-4, and exhausting the air from the upper air vent 48. Directional arrows 115 show the air travel inside the room, in and out of the light fixture. The directional air flow has option of being reversed to allow air flow through fixture, into decontamination chamber, then exit the unit in direction opposite the direction illustrated in FIG. 5. The light sources 20 provide illumination of the room.

In the preferred embodiment, the light fixture, its housing 10, and the other parts of the system may be made from metal, plastic or other materials that are commonly used for making light fixtures. However, the housing 10 may also be made from more exotic materials such as wood, glass, porcelain, or Plexiglas or other to add to the artistic factor of such light fixtures.

The light fixture may have a back-up (battery or rechargeable battery) power supply in case of a power outage at the hospital.

The light fixture may also include internal electronics (including onboard memory chips or modules, computer chips, and wiring), other internal and/or external lights (such as LED or fiber optic), and other to further enhance the usefulness and control associated with the present invention, such as for example control circuitry, time-based air sweeps, air quality sensors, voice- or sound-activated controls, and so on.

While the system and device of the present invention have been shown and described in accordance with the preferred and practical embodiments thereof, it is recognized that departures from the instant disclosure are contemplated within the spirit and scope of the present invention. Therefore, the true scope of the invention should not be limited by the abovementioned description of the preferred embodiment since other modifications may become apparent to those skilled in the art upon a study of the drawings, description, explanations, and specifications herein. Various modifications to these embodiments will be readily apparent to those skilled in the art, and the principles described herein can be applied to other embodiments without departing from the spirit or scope of the invention and the subject matter of the present invention.

The system and device of the present invention may be used not just at hospitals or health care facilities, but also other locations with increased likelihood of bacteria or other pathogen accumulation, such as any common area where people congregate or spend time, public places, buses, trains, aircraft, spacecraft, ships, emergency vehicles, transportation vehicles, or any other area with a particular emphasis on sanitary facilities or decontamination.

What is claimed is:

1. A wall-mounted light fixture, comprising:
   a. A housing of the light fixture, having a substantially-vertical mounting wall with an upper edge and a lower edge, a substantially-horizontal top wall connected to the mounting wall along the upper edge, a substantially-horizontal bottom wall connected to the lower edge, and a front wall connected to the top wall and the bottom wall along their respective edges opposite to connections at the upper edge and the lower edge so that the front wall is substantially facing a room when the light fixture is installed, said mounting wall, top wall, bottom wall and front wall defining an internal space, wherein the housing is adapted to be placed, attached or mounted onto the wall inside the room by securing means coupled with the mounting wall so that the top wall is below room ceiling level;
   b. One or more external light sources coupled substantially flush with at least one of the top wall and the front wall, said one or more external light sources being selectively operable to illuminate the room;
   c. A plurality of substantially parallel plates disposed in the internal space, defining a decontamination chamber for air flow therebetween;
   d. At least one internal decontamination source adapted to be placed, attached or mounted into the decontamination chamber; and
   e. One or more fan for driving air through the decontamination chamber, wherein the air is in direct contact with the at least one internal decontamination source and is decontaminated by the at least one internal decontamination source when the air passes through the decontamination chamber.

2. The light fixture of claim 1, wherein the least one internal decontamination source is placed, attached or mounted on at least one of the plurality of substantially parallel plates.

3. The light fixture of claim 1, further comprising at least one aperture in the top wall or the front wall selectively operable as an air intake aperture or an air exhaust aperture, said aperture cooperating with the one or more fan for driving air.

4. The light fixture of claim 1, further comprising at least one air exhaust aperture in the top wall cooperating with the one or more fan for driving air.

5. The light fixture of claim 1, wherein the least one internal decontamination source is selectively operable to decontaminate air.

6. The light fixture of claim 1, further comprising at least one selectively operable external decontamination source disposed on the front wall.

7. The light fixture of claim 1, wherein the securing means are removably attachable.

8. The light fixture of claim 1, further comprising a maintenance panel in the front wall to access the internal space.

9. The light fixture of claim 1, further comprising at least one air filter coupled with the one or more fan for driving air.

10. The light fixture of claim 9, further comprising a vent access panel to access the at least one air filter.

11. The light fixture of claim 10, wherein the vent access panel is removable or hinged to provide access to the internal space for repair and maintenance.

12. The light fixture of claim 1, wherein one or more of the housing, the walls, the securing means, the one or more external light sources, the plurality of substantially parallel plates, the at least one internal decontamination source, and the one or more fan for driving air are modular.

13. The light fixture of claim 1, further comprising a room occupancy sensor or motion sensor for activating the one or more external light sources or the at least one internal decontamination source.

14. The light fixture of claim 1, wherein the at least one internal decontamination source is selected from a group consisting from germicidal light, ultraviolet light, ultraviolet-C light (UV-C), sonic source, and ultrasonic source.

15. The light fixture of claim 1, further comprising an internal back up power source to power the one or more external light sources or the at least one internal decontamination source.

16. The light fixture of claim 14, wherein the least one internal decontamination source is an LED-based ultraviolet light.

17. The light fixture of claim 1, wherein the at least one internal decontamination source is selected from a group consisting from germicidal light, ultraviolet light, ultraviolet-C light (UV-C), sonic source, and ultrasonic source.

18. The light fixture of claim 1, further comprising an internal back up power source to power the one or more external light sources or the at least one internal decontamination source.

19. The light fixture of claim 17, wherein the least one internal decontamination source is an LED-based ultraviolet light.

20. A wall-mounted light fixture, comprising:
   a. A light fixture housing having a substantially-vertical mounting wall with an upper edge and a lower edge, a substantially horizontal top wall connected to the mounting wall at the upper edge, a substantially horizontal bottom wall connected to the mounting wall at the lower edge, and a substantially vertical front wall opposite to the mounting wall, said front wall being connected to the top wall and the bottom wall along their respective edges opposite to connections at the upper edge and the lower edge, said walls defining an internal space therebetween, wherein the housing is adapted to be placed, attached or mounted onto the wall inside a room by securing means coupled with the mounting wall so that the top wall is below room ceiling level;
   b. A top external light source coupled substantially flush with the top wall, said top external light source being selectively operable to illuminate the room;
   c. Air intake means disposed in the internal space;
   d. An air intake aperture in the bottom wall or the front wall cooperatively coupled with the air intake means;
   e. Air exhaust means disposed in the internal space;
   f. An air exhaust aperture in the top wall or the front wall cooperatively coupled with the air exhaust means;
   g. A plurality of substantially parallel plates disposed in the internal space, defining a decontamination duct for air flow therebetween; and
   h. At least one internal decontamination source adapted to be placed, attached or mounted into the decontamination duct, wherein the air intake means draw air through the air intake aperture and drive the air through the decontamination duct where the air is in direct contact with the at least one internal decontamination source and is decontaminated by the at least one internal decontamination source, and wherein the air exhaust means draw air from the decontamination duct and expel the air through the air exhaust aperture.

21. The light fixture of claim 20, wherein the least one internal decontamination source is placed, attached or mounted on at least one of the plurality of substantially parallel plates.

22. The light fixture of claim 20, further comprising at least one selectively operable external decontamination source disposed on the front wall or the bottom wall.

23. The light fixture of claim 20, further comprising a maintenance panel in the front wall or the bottom wall to access the internal space.

24. The light fixture of claim 20, wherein the at least one internal decontamination source is selected from a group consisting from germicidal light, ultraviolet light, ultraviolet-C light (UV-C), sonic source, and ultrasonic source.

25. The light fixture of claim 20, wherein the air intake means and the air exhaust means are selectively capable of simultaneously enabling reverse air flow direction, wherein the air exhaust means draw the air from the air exhaust aperture and the air intake means exhaust the air through the air intake aperture.

26. The light fixture of claim 20, further comprising one or more of a mounted indicator to provide an audible or visible alert if a component fails or requires maintenance and a monitoring system communicating the operating status of the light fixture to an off-site location monitoring station.

27. The light fixture of claim 25, wherein the least one internal decontamination source is an LED-based ultraviolet light.

28. The light fixture of claim 20, further comprising a bottom external light source coupled substantially flush with the bottom wall or a front external light source coupled substantially flush with the front wall, said bottom external light source or said front external light source being selectively operable to illuminate the room.

29. The light fixture of claim 28, wherein the top external light source, the bottom external light source, or the front external light source is selectively operable by a patient or a person near the light fixture to control visible directional lighting.

30. A wall-mounted light fixture, comprising:
   a. A housing of the light fixture having a substantially-vertical mounting wall with an upper edge and a lower edge, a substantially-horizontal top wall connected to the mounting wall along the upper edge, and an angled front wall connected to the lower edge, wherein the top wall and the front wall are connected along their respective edges opposite to connections at the upper edge and the lower edge so that the front wall is substantially facing a room when the light fixture is installed, said mounting wall, top wall and front wall defining an internal space, wherein the housing is adapted to be placed, attached or mounted onto the wall inside the room by securing means coupled with the mounting wall so that the top wall is below room ceiling level;
   b. One or more external light sources coupled substantially flush with at least one of the top wall and the front wall, said one or more external light sources being selectively operable to illuminate the room;
   c. A plurality of substantially parallel plates disposed in the internal space, defining a decontamination chamber for air flow therebetween;
   d. At least one internal decontamination source adapted to be placed, attached or mounted into the decontamination chamber; and
   e. One or more fan for driving air through the decontamination chamber, wherein the air is in direct contact with the at least one internal decontamination source and is decontaminated by the at least one internal decontamination source when the air passes through the decontamination chamber.

31. The light fixture of claim 30, wherein the least one internal decontamination source is placed, attached or mounted on at least one of the plurality of substantially parallel plates.

32. The light fixture of claim 30, further comprising at least one aperture in the top wall or the front wall selectively operable as an air intake aperture or an air exhaust aperture, said aperture cooperating with the one or more fan for driving air.

33. The light fixture of claim 30, further comprising at least one air exhaust aperture in the top wall cooperating with the one or more fan for driving air.

34. The light fixture of claim 30, wherein the least one internal decontamination source is selectively operable to decontaminate air.

35. The light fixture of claim 30, further comprising at least one selectively operable external decontamination source disposed on the front wall.

36. The light fixture of claim 30, wherein the securing means are removably attachable.

37. The light fixture of claim 30, further comprising a maintenance panel in the front wall to access the internal space.

38. The light fixture of claim 30, further comprising at least one air filter coupled with the one or more fan for driving air.

39. The light fixture of claim 38, further comprising a vent access panel to access the at least one air filter.

40. The light fixture of claim 39, wherein the vent access panel is removable or hinged to provide access to the internal space for repair and maintenance.

41. The light fixture of claim 30, wherein one or more of the housing, the walls, the securing means, the one or more external light sources, the plurality of substantially parallel plates, the at least one internal decontamination source, and the one or more fan for driving air are modular.

42. The light fixture of claim 30, further comprising a room occupancy sensor or motion sensor for activating the one or more external light sources or the at least one internal decontamination source.

\* \* \* \* \*